United States Patent [19]

Berg et al.

[11] Patent Number: 4,572,734

[45] Date of Patent: Feb. 25, 1986

[54] PLANT GROWTH-REGULATING AGENTS

[75] Inventors: Dieter Berg; Wolf Reiser, both of Wuppertal; Klaus Lürssen, Bergisch Gladbach, all of Fed. Rep. of Germany

[73] Assignee: Bayer Aktiengesellschaft, Leverkusen, Fed. Rep. of Germany

[21] Appl. No.: 603,461

[22] Filed: Apr. 24, 1984

[30]     Foreign Application Priority Data

Apr. 29, 1983 [DE]   Fed. Rep. of Germany ....... 3315593

[51] Int. Cl.[4] ............................................. A01N 41/06
[52] U.S. Cl. ........................................... 71/72; 71/103
[58] Field of Search ..................................... 71/72, 103

[56]                References Cited

U.S. PATENT DOCUMENTS 4,093,445  6/1978  Arneklev et al. ...................... 71/100
4,113,463  9/1978  Oshio et al. .............................. 71/76

OTHER PUBLICATIONS

Ivan C. Popoff, "Hydroxybenzenesulfonyl Fluorides and Their Plant Desiccation Activity", J. Agr. Food Chem., 7-8 '69, pp. 810-817.
Popoff et al., Chem. Abst. vol. 71 (1969) 59946g.

*Primary Examiner*—Catherine L. Mills
*Attorney, Agent, or Firm*—Sprung, Horn, KraMER & Woods

[57]              ABSTRACT

A process for regulating the growth of plants is described by applying to the plants or their habitat a plant growth regulatingly effective amount of a 3,5-dichloro-2-hydroxy-benzenesulphonamide of the formula

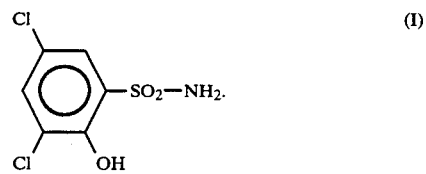

The compound is especially useful as a defoliant and a desiccant for cotton plants.

4 Claims, No Drawings

PLANT GROWTH-REGULATING AGENTS

The present invention relates to the use of 3,5-dichloro-2-hydroxy-benzenesulphonamide, as a plant growth regulator.

3,5-Dichloro-2-hydroxy-benzenesulphonamide, and its use as an acaricide and herbicide, are already known (see DRP 733,514, Houben-Weyl "Methoden der organischen Chemie" [Methods of Organic Chemistry], Volume IX, page 607, 4th Edition 1955, Tetrahedron Letters 1972, 251–254, DE-OS [German Published Specification] No. 2,246,403, and Phosphorous and Sulfur 6, 413–419 (1979)).

However, the use of this compound for regulating plant growth has not been described to date.

Furthermore, it is known that a large number of sulphonanilides possess plant growth-regulating properties (see DE-OS [German Published Specification] No. 2,845,997). Thus, for example, methanesulphonic acid 3-chloro-4-chlorodifluoromethylsulphonylanilide and chloromethanesulphonic acid 3-chloro-4-methoxy-anilide can be employed as plant growth regulators. However, the activity of these compounds is not always adequate.

It has now been found that the known compound 3,5-dichloro-2-hydroxy-benzenesulphonamide of the formula

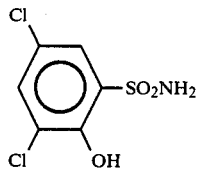

is very suitable for regulating plant growth.

It is to be regarded as extremely surprising that 3,5-dichloro-2-hydroxy-benzenesulphonamide, which can be used according to the invention, possesses better plant growth-regulating properties than methanesulphonic acid 3-chloro-4-chlorodifluoromethylsulphonylanilide and chloromethanesulphonic acid 3-chloro-4-methoxyanilide, which are constitutionally similar, previously known active compounds having the same mode of action.

As already mentioned above, the active compound of formula (I) which can be used according to the invention is known (see Houben-Weyl "Methoden der organischen Chemie" [Methods of Organic Chemistry], Vol. IX, page 607, 4th Edition 1955, and DE-OS [German Published Specification] No. 2,246,403). 3,5-Dichloro-2-hydroxy-benzenesulphonamide is obtained, for example, by treating 2,4-dichloro-phenylene-o-sulphonylide with ammonia in an autoclave, or by reacting 3,5-dichloro-2-hydroxybenzene-sulphonyl chloride with ammonia in the presence of tetrahydrofuran.

The active compound of the formula (I) which can be used according to the invention engages in the metabolism of the plants and can therefore be employed as a growth regulator.

Experience to data of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired, without damaging them.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. In the case of cotton, prevention of resprouting after defoliation is of particular interest. Defoliation of the plants can also be carried out to lower the transpiration of plants before they are transplanted.

3,5-Dichloro-2-hydroxybenzenesulphonamide of the formula (I), which can be used according to the invention, can preferably be employed for the defoliation of plants. It is particularly suitable for defoliation and for the inhibition of resprouting in cotton.

The active compound which can be used according to the invention can be converted to the customary formulations, such as solutions, emulsions, suspensions, powders, foams, pastes and ULV formulations.

These formulations are produced in known manner, for example by mixing the active compound with extenders, that is, liquid solvents, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane and paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents such as dimethylformamide and dimethylsulphoxide, as well as water. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysation products. As dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound which can be used according to the invention can be present in the formulations as a mixture with other known active compounds, such as fungicides, insecticides, acaricides and herbicides, and also as mixtures with fertilisers and other growth regulators.

The active compound can be used as such, in the form of its formulations or as the use forms prepared therefrom, such as ready-to-use solutions, emulsifiable concentrates, emulsions, foams, suspensions, wettable powders, pastes and soluble powders. They are used in the customary manner, for example by watering, spraying, atomising, scattering, dusting, foaming, coating and the like. Furthermore, it is possible to apply the active compound in accordance with the ultra-low volume process or to inject the active compound preparation or the active compound itself into the soil. It is also possible to treat the seeds of the plant.

The amounts applied can be varied within a substantial range. In general, 0.01 to 50 kg, preferably 0.05 to 10 kg, of the active compound are employed per hectare of soil surface.

As regards the time of application, the rule is that the growth regulators are applied within a preferred period of time, the exact definition of which depends on the climatic and vegetative circumstances.

The use of 3,5-dichloro-2-hydroxy-benzenesulphonamide as a plant growth regulator is illustrated by the example which follows.

EXAMPLE A

Defoliation and desiccation of the leaves of cotton

Solvent: 30 parts by weight of dimethylformamide

Emulsifier: 1 part by weight of polyoxyethylene sorbitane monolaurate

To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:

0 denotes no desiccation of leaves, no shedding of leaves

+ denotes slight desiccation of the leaves, slight shedding of leaves

++ denotes severe desiccation of the leaves, severe shedding of leaves

+++ denotes very severe desiccation of the leaves, very severe shedding of the leaves.

Active compounds, active compound concentration and experimental results are given in the Table below.

TABLE A

| Defoliation and desiccation of the leaves of cotton | | |
|---|---|---|
| Active compound | Concentration in % | Action |
| Untreated control | — | =0 |
| ![Cl, Cl, OH, SO2—NH2 structure] | 0.05 | ++ |
| Comparative substances: | | |
| ClF2C—SO2—(Cl)—NH—SO2—CH3 (disclosed in DE-OS [German Published Specification] 2,845,997) | 0.05 | 0 |
| CH3O—(Cl)—NH—SO2—CH2Cl (disclosed in DE-OS [German Published Specification] 2,845,997) | 0.05 | 0 |
| NCS—(Cl)—NH—SO2—CH2Cl (disclosed in DE-OS [German Published Specification] 2,845,997) | 0.05 | 0 |
| CH3SO2—(Cl)—NH—SO2—CH3 (disclosed in DE-OS [German Published Specification] 2,845,997) | 0.05 | 0 |
| CH3SO—(Cl)—NH—SO2—CH3 (disclosed in DE-OS [German Published Specification] 2,845,997) | 0.05 | 0 |

When 3,5-dichloro-2-hydroxy-benzenesulphonamide was used, in particular inhibition of resprouting was observed, in addition to the good action in defoliating and desiccating the leaves of the cotton plants.

What is claimed is:

1. A process for defoliating and desiccating cotton plants which comprises applying to the cotton plants or to their habitat and effective amount of 3,5-dichloro-2-hydroxy-benzenesulphonamide of the formula

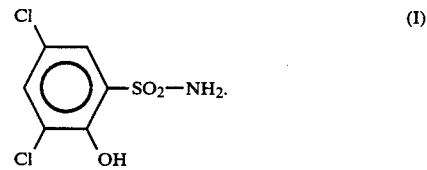

2. A process according to claim 1 wherein said 3,5-dichloro-2-hydroxy-benzenesulphonamide is applied to said cotton or its habitat in admixture with an extender or surface active substance.

3. A process according to claim 1 wherein said 3,5-dichloro-2-hydroxy-benzenesulphonamide is applied in an amount of 0.01 to 50 kg per hectare of soil surface.

4. A process according to claim 1 wherein said 3,5-dichloro-2-hydroxy-benzenesulphonamide is applied in an amount of 0.05 to 10 kg per hectare of soil surface.

* * * * *